United States Patent
Ando et al.

(10) Patent No.: US 7,530,972 B2
(45) Date of Patent: May 12, 2009

(54) ABSORBENT ARTICLE AND PROCESS OF PRODUCING THE SAME

(75) Inventors: Kenji Ando, Tochigi (JP); Takuo Yanashima, Tochigi (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 10/784,197

(22) Filed: Feb. 24, 2004

(65) Prior Publication Data

US 2004/0230171 A1    Nov. 18, 2004

(30) Foreign Application Priority Data

Feb. 25, 2003    (JP)    ............... 2003-048136

(51) Int. Cl.
*A61F 13/15*    (2006.01)
(52) U.S. Cl. .................. 604/385.27; 604/385.24; 604/385.26; 604/385.29; 604/385.3
(58) Field of Classification Search ............ 604/385.24, 604/385.26, 385.27, 385.29, 385.3, 385.01
See application file for complete search history.

(56) References Cited

U.S. PATENT DOCUMENTS

| | | | | |
|---|---|---|---|---|
| 5,330,458 | A * | 7/1994 | Buell et al. ............. | 604/385.24 |
| 6,264,639 | B1 * | 7/2001 | Sauer .................. | 604/385.101 |
| 6,307,119 | B1 | 10/2001 | Cammarota et al. | |
| 2001/0031954 | A1 * | 10/2001 | Jordan et al. ........... | 604/385.01 |
| 2004/0030317 | A1 * | 2/2004 | Torigoshi ................ | 604/385.27 |

FOREIGN PATENT DOCUMENTS

| | | |
|---|---|---|
| EP | 1078620 A2 | 2/2001 |
| EP | 1222907 A2 | 7/2002 |
| EP | 1226802 A2 | 7/2002 |
| JP | 2002-159528 | * 11/2000 |
| JP | 2001-478 A | 1/2001 |
| JP | 2001-61890 A | 3/2001 |
| JP | 2001-145666 A | 5/2001 |
| JP | 2002-95692 A | 4/2002 |
| JP | 2002-253605 A | 9/2002 |
| JP | 2002-272783 A | 9/2002 |

OTHER PUBLICATIONS

English language abstract of JP 03090602 (Apr. 16, 1991).
English language abstract of JP 2002272783 (Sep. 24, 2002).
English language abstract of JP 2002273808 (Sep. 25, 2002).

* cited by examiner

*Primary Examiner*—Jacqueline F. Stephens
(74) *Attorney, Agent, or Firm*—Birch, Stewart, Kolasch & Birch, LLP

(57) ABSTRACT

The absorbent article has an outer sheet that provides an outer surface of the absorbent article, an inner sheet disposed on the inner side of the outer sheet, and elastic members for making below-waist gathers disposed between the two sheets. A patterned sheet is disposed between the outer and inner sheets such that the pattern of the patterned sheet may be seen through the outer sheet from the outside of the diaper. The elastic members for below-waist gathers each have a portion contributory to elastic extensibility and contractibility in the regions outside the lateral sides of the patterned sheet and a portion substantially non-contributory to elastic extensibility and contractibility in the region inside the lateral sides of the patterned sheet. The latter portion of the elastic member is disposed between the patterned sheet and the inner sheet and preferably is kept out of sight from the outside.

14 Claims, 6 Drawing Sheets

ABSORBENT ARTICLE AND PROCESS OF PRODUCING THE SAME

This Nonprovisional application claims priority under 35 U.S.C. §119(a) on Patent Application No(s). 2003-048136 filed in JAPAN on Feb. 25, 2003, the entire contents of which are hereby incorporated by reference.

FIELD OF THE INVENTION

The present invention relates in general to an absorbent article with a pattern and a process of producing the same.

BACKGROUND OF THE INVENTION

Pull-on diapers (also called pants type diapers) having a plurality of elastic members laterally disposed in the below-waist portion thereof, which is to be located around a wearer's below-waist portion, to make below-waist gathers are known. Among recently proposed pull-on diapers are those having below-waist gathers not around the whole circumference below the waist but only in both side portions. Such side gathers are formed by cutting elastic members disposed in the below-waist portion at the proximity of the widthwise middle of the front portion (the portion to be located on the wearer's stomach side) and/or the rear portion (the portion to be located on the wearer's back side).

For example, JP-A-2001-478 discloses a disposable diaper having a laminate for snug-fit gathers which is composed of a pair of nonwoven fabric sheets and elastic members for below-waist gathers disposed between the sheets. The laminate has the elastic members fixed over the whole width thereof except the widthwise middle portion, and the elastic members have been cut in that widthwise middle portion. Since the elastic members, held in between the two nonwoven fabric sheets, have been cut in the middle of the laminate, a reinforcing sheet is bonded to one of the nonwoven fabric sheets to compensate for the shortage of laminate strength due to the cutting. The reinforcing sheet is further covered with a backsheet. The publication additionally mentions that a patterned sheet can be used as the reinforcing sheet.

JP-A-2002-272783 proposes a disposable pull-on diaper having an outer laminate sheet composed of two nonwoven fabric sheets and elastic members for below-waist gathers disposed therebetween. In an embodiment of the diaper, a pattern of a backsheet disposed on the inner side of the outer laminate sheet can be seen through the outer laminate sheet.

The above-described conventional disposable diapers encounter with the following problems. In the diaper of JP-A-2001478, the cut portions of the elastic members are covered with three sheets on the outer side thereof. That is, the diaper involves use of an increased number of constituent members, which results in increased cost. The problem of JP-A-2002-272783 is that the pattern cannot be clearly seen from the outside because it is covered with two nonwoven fabric sheets.

JP-A-2001-61890 suggests that the cut ends of elastic members for below-waist gathers, if noticeable to the naked eye, can be hidden by providing a hiding member on the outer side of the below-waist elastic members. The publication does not give specific description about the hiding method nevertheless.

SUMMARY OF THE INVENTION

The absorbent article according to the present invention has an outer sheet that provides an outer surface of the absorbent article, an inner sheet disposed on the inner side of the outer sheet, and a plurality of elastic members for making below-waist gathers disposed between the two sheets. The absorbent article has a front portion that is located on the wearer's stomach side while worn and a rear portion that is located on the wearer's back side. A patterned sheet is disposed between the outer and inner sheets in the widthwise middle area on the front portion and/or the rear portion. The elastic members for below-waist gathers each have a portion contributory to elastic extensibility and contractibility and a portion substantially non-contributory to elastic extensibility and contractibility. The former portion of the elastic member is disposed in the regions outside the lateral sides of the patterned sheet, and the latter portion is in the region inside the lateral sides of the patterned sheet. The latter portion of the elastic member is disposed between the patterned sheet and the inner sheet.

The process of producing one embodiment of an absorbent article according to the present invention is a process for producing such an absorbent article in which the above-described portion substantially non-contributory to extensibility and contractibility are cut ends and/or a fragment (a cut piece) resulting from cutting the elastic members. The process includes the steps of disposing cut patterned sheets at an interval on a running outer sheet of continuous length, continuously introducing elastic members of continuous length between the outer sheet with the patterned sheets on and a running inner sheet of continuous length, bonding the inner sheet to the patterned sheet side of the outer sheet to form a laminate, and cutting the elastic members of continuous length by pressing a pressing member having projections against the region where the patterned sheet is disposed.

BRIEF DESCRIPTION OF THE DRAWINGS

The present invention will be more particularly described with reference to the accompanying drawings, in which.

DETAILED DESCRIPTION OF THE INVENTION

The present invention provides an absorbent article which has a pictorial pattern clearly seen from the outside and can be produced from a reduced number of constituent members at reduced cost and a process of making preferred embodiment of an absorbent article.

The present invention will be described by referring to its preferred embodiments.

Figure 1:
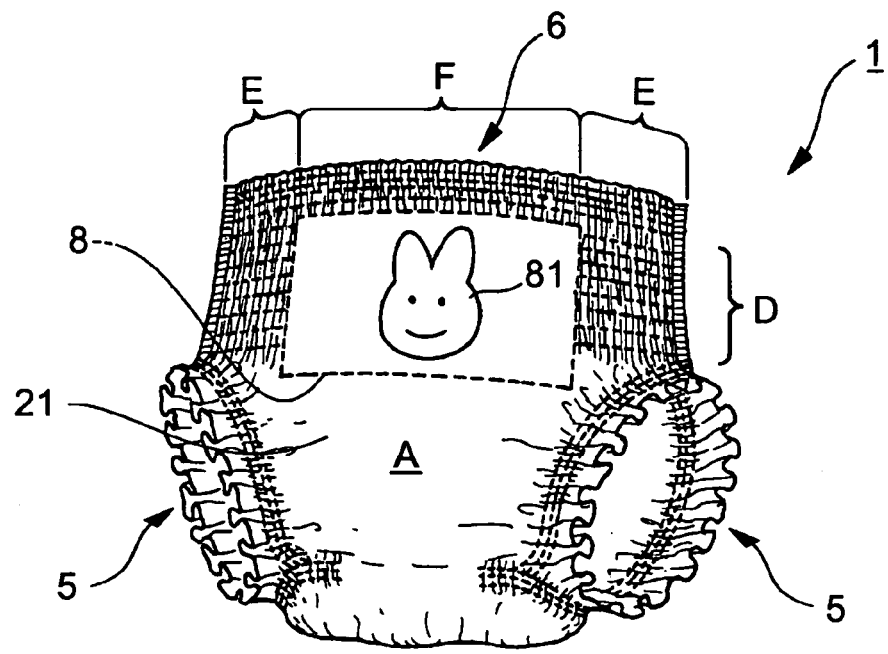
FIG. 1 is a perspective of a disposable diaper as an embodiment of the present invention.
Figure 2:
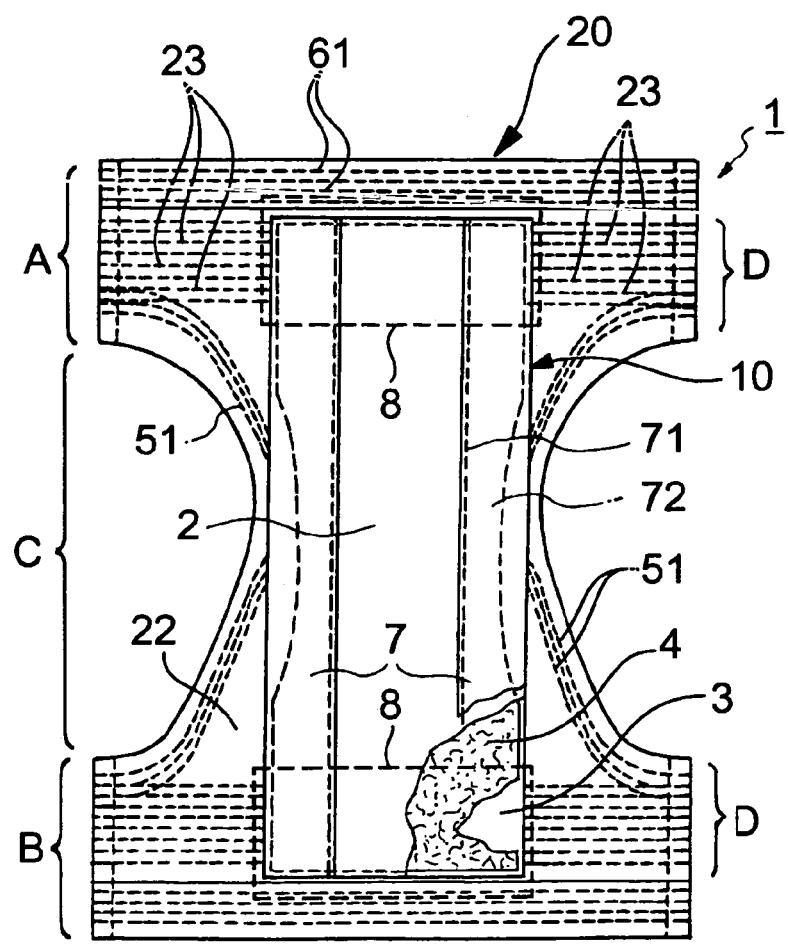
FIG. 2 is a plan of the disposable diaper shown in FIG. 1 in its opened and stretched flat state.

The present invention provides in its first embodiment a disposable pull-on diaper for infants. The disposable diaper 1 according to the first embodiment shown in FIGS. 1 and 2 has a liquid permeable topsheet 2, a liquid impermeable backsheet 3, and a liquid retentive absorbent member 4. The disposable diaper 1 is sectioned into a front portion A that is to be located on the stomach side of a wearer, a rear portion B that is to be located on the back side of a wearer, and a crotch portion C positioned between the front portion A and the back portion B.

The lateral edges of the front portion A and those of the rear portion B are joined together by any known means, such as heat sealing, high frequency sealing or ultrasonic sealing, to form a pants type diaper having a pair of leg openings 5 and a waist opening 6.

The disposable diaper 1 is composed of an absorbent body 10 containing a liquid retentive absorbent member 4 and an exterior laminate 20 which is disposed on the outer side of the absorbent body 10 (i.e., on the side opposite the wearer's side) to fixedly support the absorbent body 10.

The absorbent member 4 is interposed between the topsheet 2 and the backsheet 3. These three members are united in their thickness direction to form the absorbent body 10. The absorbent body 10 has an oblong rectangular shape. The absorbent body 10 is bonded to the central part of the exterior laminate 20 by known joining means with its longitudinal direction in agreement with the direction extending from the front portion A to the rear portion B via the crotch portion C (hereinafter referred to as a longitudinal (length) direction of a diaper). An oblong sheet 72 having an elastic member 71 is disposed on both long sides of the absorbent body 10 to provide a pair of standing cuffs 7.

A leg elastic member 51 and a waist elastic member 61 are arranged along the periphery of the leg openings 5 and of the waist opening 6, respectively, to form leg gathers and a waist gather.

Figure 3:
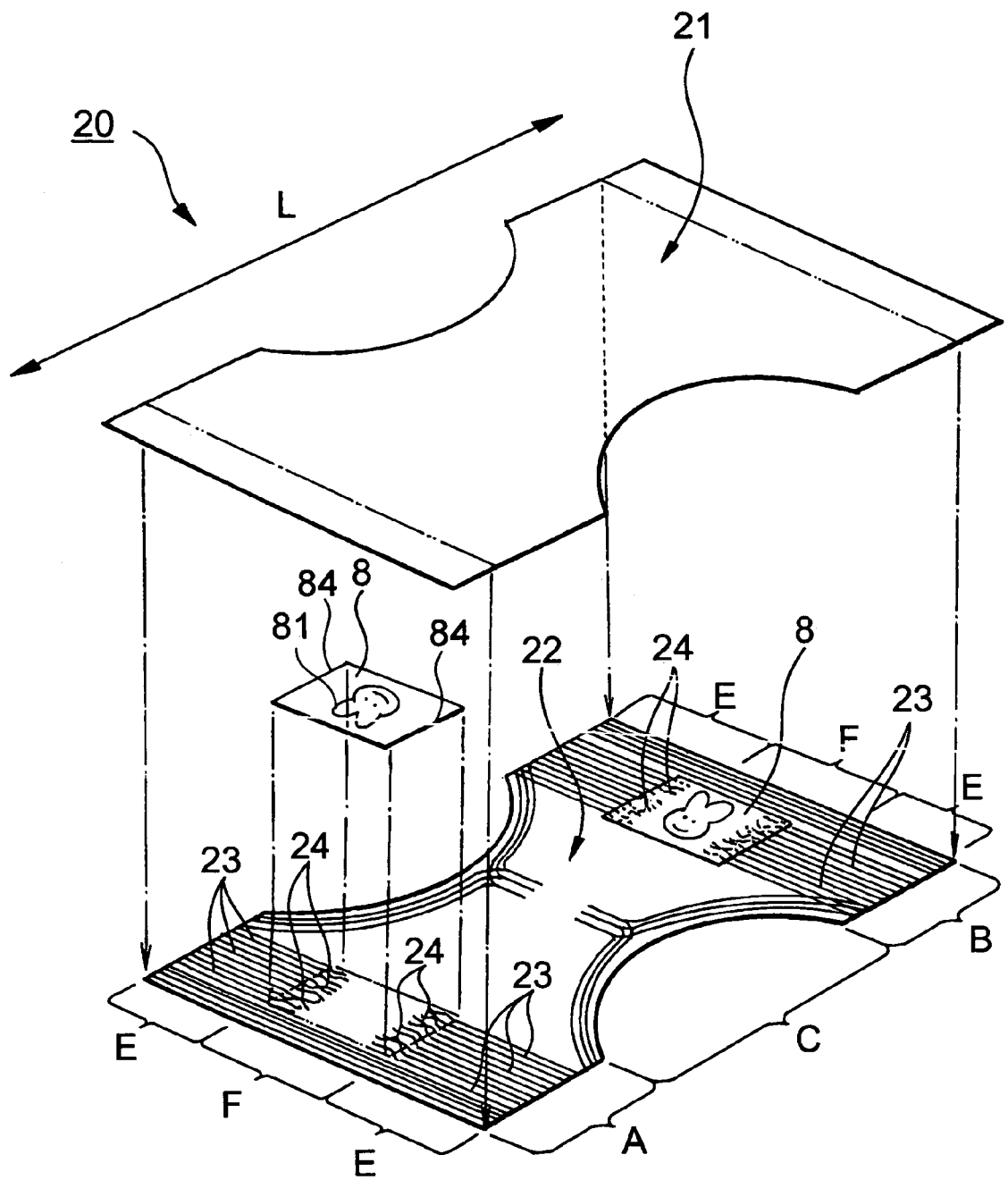
FIG. 3 is an exploded perspective view of the exterior laminate of the disposable diaper shown in FIG. 1.

As shown in FIG. 3, the exterior laminate 20 has an outer sheet 21 serving as the outer surface of the diaper 1 (the side opposite to a wearer's side), an inner sheet 22 adjoining the outer sheet 21, and a plurality of elastic members arranged between these two sheets to make below-waist gathers (hereinafter referred to as "below-waist elastic members").

The below-waist elastic members 23 are arranged in the below-waist portion D (see FIG. 1) of the front portion A and/or the rear portion B in the circumferential direction to provide the below-waist portion D with extensible and contractible gathers. In the present embodiment, the below-waist elastic members 23 are placed in both below-waist portions D of the front portion A and the rear portion B. The below-waist portion D as referred to herein is a portion above the crotch portion C (the portion with leg openings on each side) and below the waist portion where the waist elastic member 61 is disposed (see FIG. 2).

Both the outer sheet 21 and the inner sheet 22 have a sandglass shape with the longitudinal middle portion narrowed as depicted in FIG. 3. The outer sheet 21 is longer than the inner sheet 22, extending outward from the longitudinal ends of the inner sheet 22. The extended parts of the outer sheet 21 are folded back and fixed to the inner side of the inner sheet 22.

The inner sheet 22 has a function of fixing the below-waist elastic members 23 on the inner side (the side nearer to a wearer) of the outer sheet 21. As in the present embodiment, it is preferred for the inner sheet 22 cover the entire area of the inner side of the outer sheet 21 to fix the leg elastic members 51 and the waist elastic member 61 as well as the below-waist elastic members 23. It is possible for the inner sheet 22 to be disposed only on the below-waist portion D of the front portion A and/or the below-waist portion D of the rear portion B.

A rectangular patterned sheet 8 with a pattern 81 is inserted between the outer sheet 21 and the inner sheet 22 in the widthwise middle areas each of the front portion A and the rear portion B. The pattern 81 of each patterned sheet 8 can be seen through the outer sheet 21 from the outside of the diaper 1.

In this particular embodiment, the patterned sheet 8 and the below-waist elastic members are provided in both the front portion A and the rear portion B. The way of arranging the patterned sheet 8 and the below-waist elastic members 23 in the rear portion B is the same as in the front portion A For the sake of simplicity, the patterned sheet 8 and the below-waist elastic members 23 will be described with reference only to the front portion A. The description applies also to the rear portion B.

Figure 6A:
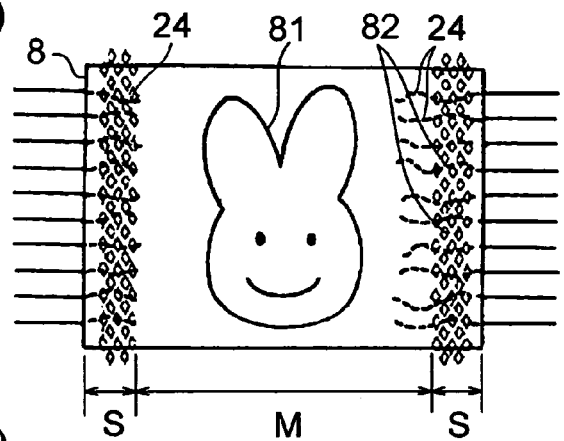
FIG. 6(a), FIG. 6(c), and FIG. 6(d) each show a preferred pattern of arranging dots corresponding to projections (or projections themselves)
Figure 6B:
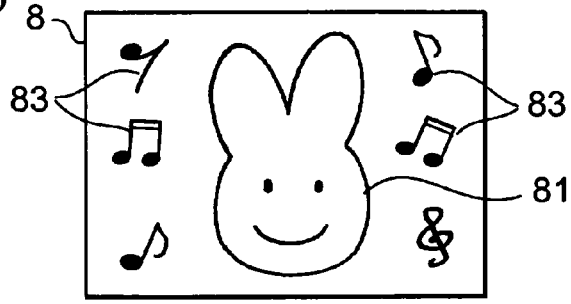
FIG. 6(b) is an illustration for explaining the term "main pattern"
Figure 6C:
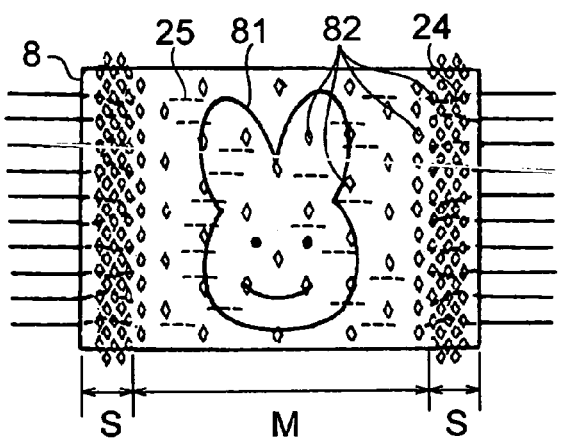
Figure 6D:
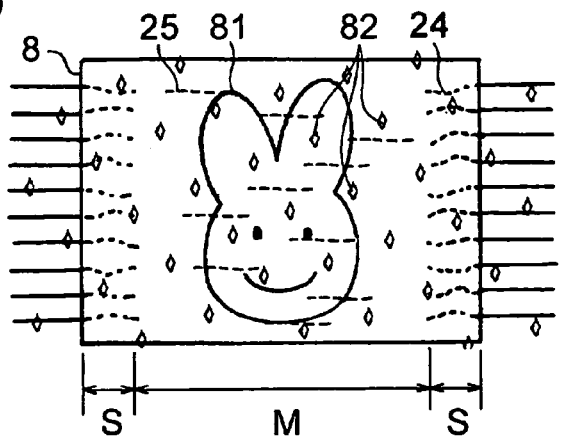

The below-waist elastic members 23 are arranged parallel to one another with spacing in the width direction of the front portion A (the same as the circumferential direction of the below-waist portion D). Every elastic member 23 has a portion contributory to elastic extensibility and contractibility and a portion substantially non-contributory to elastic extensibility and contractibility. The former portion of the elastic member 23 is located on each of the regions E outside the lateral sides 84 of the patterned sheet 8. The latter portion is on the region F inside the lateral sides 84 of the patterned sheet 8. The latter portion includes cut ends 24 and fragments 25 (see FIGS. 6(c) and 6(d)). In FIG. 3, the fragments 25 are not depicted.

The expression "substantially non-contributory to elastic extensibility and contractibility" as used herein includes not only the state in which the elastic member is completely released from tension and exhibits no elastic extensibility and contractibility at all but also the state in which the elastic member is slightly extensible and contractible within such a small range that does not cause the adjacent patterned sheet to generate wrinkles.

The below-waist elastic members 23 are provided over almost the whole lateral dimension of the portions E outside the lateral sides 84 of the patterned sheet 8 to exhibit lateral extensibility and contractibility in these portions. Thus, a pair of below-waist gathers are formed in the two separate portions E. Each below-waist elastic member 23 does not always need to be fixed over its total length in each portion E. It may be fixed at parts, for example, only at the lateral edges of each portion E.

Because the below-waist elastic members 23 have, in the portion F, the cut ends 24 and/or the fragments 25 which have lost their function as an elastic member, the portion F of the exterior part 20 is prevented from gathering. Accordingly, the absorbent member is also prevented from gathering, namely wrinkling and bunching. As a result, the absorbent member provides snug fit to a wearer's body and is prevented from reducing its absorbing performance and leaking.

Since the cut ends 24 and the fragments 25 of the below-waist elastic members 23 are sandwiched in between the patterned sheet 8 and the inner sheet 22, they are hardly seen from the outside, being hidden by the patterned sheet 8. It is only the outer sheet 21 that covers the patterned sheet 8. Therefore, the pattern 81 of the patterned sheet 8 can be recognized clearly through the outer sheet 21. The expression "hidden" or "kept out of sight" as used for the cut ends and fragments of elastic members does not always mean that the cut ends and fragments are completely hidden from sight, which is desirable, and includes the state in which they are less perceptible to the eye than in the absence of the patterned sheet 8.

Figure 4:
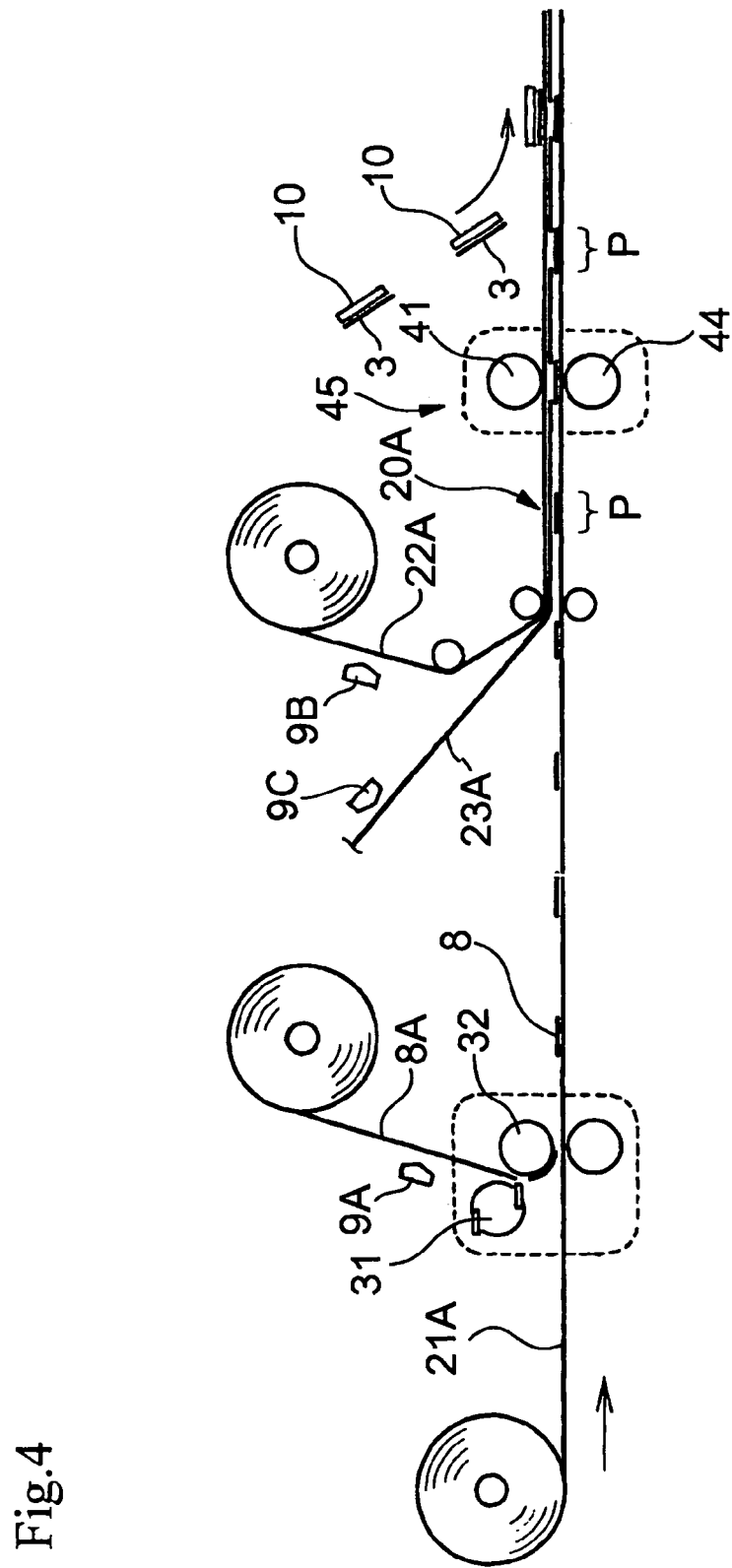
FIG. 4 schematically illustrates a preferred process of producing the disposable diaper of FIG. 1.

A preferred process of producing the disposable diaper 1 will then be described by way of FIG. 4.

A continuous sheet 21A for an outer sheet 21 is unwound from the stock roll. Patterned sheets 8 are put on the continuously running sheet 21A at a prescribed spacing.

The width of the stock sheet 21A is the same as the length L of the outer sheet 21 (see FIG. 3). The patterned sheets 8 are successively disposed on the running stock sheet 21A; two patterned sheets 8 at a time, each on one of two sites spaced in the width direction of the stock sheet 21A. That is, one patterned sheet 8 on the site corresponding to the below-waist portion D of the front portion A, and the other on the site corresponding to the below-waist portion D of the rear portion B. While not shown, the patterned sheets 8 for the front and rear portions A and B are fed from a common stock roll of a stock patterned sheet 8A. Use of a common stock roll for feeding two patterned sheets 8 at a time simplifies the feeding equipment, minimizes the time loss involved in exchanging the stock rolls, and facilitates material management. The stock patterned sheet 8A has printed patterns for the front and rear portions A and B. The stock patterned sheet 8A of continuous length unrolled from the stock roll is slit at almost the middle of the cross direction (CD) into two strips, which are then fabricated by cutting to lengths and at predetermined positions into patterned sheets 8 for the front and rear portions A and B. The trimmed patterned sheet 8 generally has a rectangular shape, which produces no trimming waste, but may have various shapes according to the design.

Cutting the strip to lengths is performed by feeding the sheet (strips) at a constant unrolling speed and forcing a cutter to the running strips at a given time interval. Cutting the strip at predetermined positions is carried out by detecting the position of the strip, comparing the position of the cutter with the position of the strip, estimating the position of the strip at the time when it is cut, and finely controlling the phase of the cutter or the unrolling speed so that the strip may be cut at the prescribed positions.

The cutter position is usually detected with a proximity switch or an encoder. A sensor is used to detect the pattern position of the strip. The patterned sheet is provided with a registration mark or an equivalent design for allowing the sensor to stably detect the pattern, which has been printed at a given pitch, of the running strip. The position of the cutter is controlled based on the proximity signals or encoder signals and the sensor signals while in operation so that the strip may be cut at prescribed positions. In FIG. 4, numerals 31 and 32 indicate a cutter roll and an anvil roll, respectively. The two rolls have functions of cutting the stock patterned sheet to lengths and arranging the cut patterned sheets 8 with spacing.

In the next step, a plurality of below-waist elastic members 23A of continuous length are continuously fed and put in their stretched state on two sites of the continuous stock sheet 21A, one site being on the patterned sheet 8 placed on the area corresponding to the front portion A and the other site being on the other patterned sheet 8 placed on the area corresponding to the rear portion B.

A stock sheet 22A of continuous length, which becomes an inner sheet 22, is fed to cover all of the continuous below-waist elastic members 23A. The width of the stock sheet 22A for the inner sheet 22 is the same as the length of the inner sheet 22 shown in FIG. 3.

While not illustrated in FIG. 4, leg elastic members 51 and waist elastic members 61, both in continuous form, are introduced before the below-waist elastic members are covered with the stock sheet 22A. In FIG. 4, reference characters 9A, 9B, and 9C indicate adhesive applicators.

In one method of applying an adhesive, the adhesive applicator 9B continuously applies a hot-melt adhesive to substantially the entire area of the stock sheet 22A. The adhesive applicator 9C applies an adhesive to the below-waist elastic members either continuously or intermittently so as not to apply the adhesive to the parts that will be located in the region F inside the lateral sides of each patterned sheet. In the latter case of intermittent application of an adhesive, the inner sheet 22 and the outer sheet 21 are bonded together, and the materials are securely adhered to each other in the regions outside the lateral sides of each patterned sheet 8. Furthermore, the parts of the elastic members that are not coated with the adhesive are ready to be released from their stretched state when they are cut afterward.

In another method of adhesive application, the adhesive applicator 9C is not used, and the adhesive applicator 9B applies a hot-melt adhesive all over the stock sheet 22A except for the region F inside the lateral sides of each patterned sheet where the below-waist elastic members are disposed or applies the adhesive all over the stock sheet 22A except that the amount of the adhesive applied to the region F is reduced as compared with the other region. According to this method, the cost of production equipment is cut down, and the texture of the exterior laminate 20 is improved by applying no adhesive or a reduced amount of the adhesive to the region corresponding to the patterned sheet.

A pressing member 41 with projections thereon is pressed onto the regions P of the resulting exterior laminate 20 where the patterned sheets are present, whereby the below-waist elastic members 23A are cut by the projections. The number of the projections of the pressing member is at least two, preferably more, e.g., 10 or more.

The pressing member 41 used in the present embodiment is a pressing roll 41 having on its peripheral surface a pair of pressing parts 43 each having a plurality of projections 42. The pressing part 43 is a platform raised from the peripheral surface of the roll 41, and the projections 42 sticking out of the platform are adapted to be heated.

Figure 5:
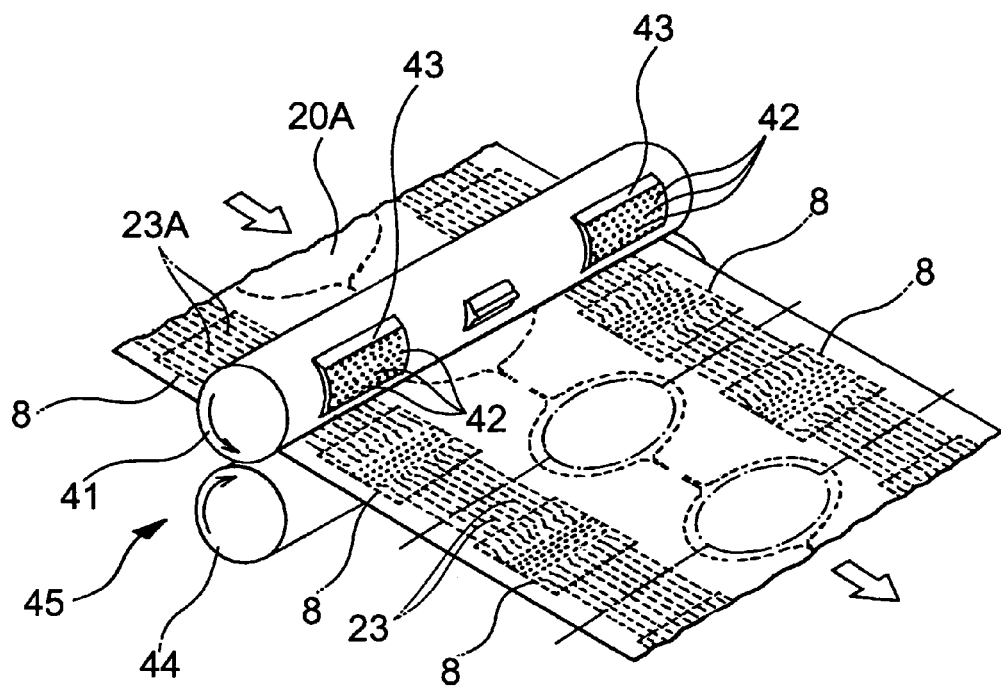
FIG. 5 is a perspective view showing below-waist elastic members of continuous length, held between the outer sheet and the patterned sheet, being cut.

As shown in FIG. 5, the pressing roll 41 is combined with an anvil roll 44 with a smooth surface placed opposite the pressing roll 41 to make an elastic member cutting unit 45. The cutting unit 45 is configured to have the exterior laminate 20 of continuous form passed between the pressing roll 41 and the anvil roll 44 and to successively press the regions P with the pressing parts 43 of the pressing roll 41. By pressing with the pressing parts 43, specifically the projections 42 regularly arranged on the pressing parts 43, the below-waist elastic members 23A of continuous length are cut at as many positions as the projections 42 while being held between the patterned sheet 8 and the inner sheet 22A of continuous length. On cutting the elastic members 23A of continuous length, cut ends 24 are produced in the region P, and fragments 25 between the cut ends 24 are left in the region P.

In cutting the below-waist elastic members of continuous length with the projections 42, the elastic members should be cut without fail, reduction in strength of the sheet materials that are also pressed should be minimized, and the pattern of the patterned sheet should be protected from damage. From all these considerations, the projections 42 are preferably dots each having a prescribed area and are preferably arrayed according to the following arrangements (1) to (3). The tip of the individual projections 42 (dots) can have various shapes, such as diamond, circle, elongated circle, ellipse, rectangle, triangle, star, and heart. The individual projections 42 and the corresponding individual dots 82 preferably have an area of 100 mm² or less, more preferably 0.001 to 30 mm². It is desirable that every elastic member of continuous length be cut at one or more positions, more desirably at two or more positions, in the region P. A projection whose area exceeds 100 mm² may damage the outer sheet 21 or the patterned sheet 8 to impair visibility of the pattern or to result in partial reduction in sheet strength, which can induce breakage of the sheets.

Arrangement (1):

Dots 82 corresponding to the projections 42 are arranged only in areas S where a main pattern 81 of the patterned sheet 8 is absent. See FIG. 6(*a*).

The dots corresponding to the projections 42 are dots resulting from pressing with the projections 42 of the pressing member 41. The dots are usually dents with a smaller thickness than the other part of the patterned sheet. In this particular embodiment, since the below-waist elastic members 23A of continuous length are cut by being pressed with a large number of heated projections 42 from the side of the inner sheet 21, the fibers under each dot become a state as if they are fused together.

The arrangement of pattern shown in FIG. 6(*a*) is a preferred example of the arrangement (1), in which dots 82 are arranged in only both side areas S where the main pattern 81 is absent.

The pattern 81 of the patterned sheet 8 includes pictorial designs, such as animals, vehicles, foods, letters, musical notes, and characters; items of labeling, such as marks indicating the front or back of the diaper, display of moisture permeability, brand name, disposal guide, etc.; and combinations thereof. Where a single shape, such as one of the above-described pictorial designs, is printed per patterned sheet, that shape is a "main pattern". Where the patterned sheet has a combination of patterns, the most user-attractive one of the combined patterns is regarded as a "main pattern".

In the patterned sheet 8 shown in FIG. 6(*b*), for example, the rabbit's face in the center is a main pattern. The notes 83 printed on both side areas S, which are obviously background areas, are also a pattern but not regarded as a "main pattern". The lateral direction in each of FIGS. 6(*a*) to 6(*d*) corresponds with the peripheral direction of the pressing roll and the width direction of a finished diaper product. This direction will sometimes be referred to simply as a (diaper) width direction.

In the arrangement (1) and the arrangements (2) and (3) hereinafter described, the dots are preferably arranged so that the below-waist elastic members of continuous length may be cut at positions on the left and right to the main pattern 81, e.g., in each of the side areas S. In other words, it is desirable to minimize the overlap of dots on the main pattern in order not to impair the sharp visibility of the pattern. In the present embodiment, pressing with the projections is conducted with due consideration for minimizing the overlap on the main pattern. The positions of the projections can be changed freely according to the position of the main pattern. For example, where a main pattern is arranged on both side areas of the patterned sheet, the projections can be applied to the central area.

Arrangement (2):

Dots 82 corresponding to projections 42 are formed in both the area M where the main pattern of a patterned sheet 8 exists and both the side areas S where the main pattern does not exist. The total dot area ratio in the area M is smaller than that in the side areas S. See FIG. 6(*c*).

FIG. 6(*c*) represents a preferred example of the arrangement (2). Dots 82 are arranged in both side areas S where no main pattern exists at a high area ratio, whereas they are arranged in the middle area M where the main pattern exists at a lower area ratio than in the side areas S.

In the dot pattern shown in FIG. 6(*c*), the average total contact line length in the middle area M having the main pattern 81 is shorter than in each of the side areas S having no main pattern. The term "average total contact line length" as used herein means an average of the total length of the dots (projections) present on a nip (line of contact) between the pressing roll and the anvil roll in the axial direction of the rolls.

The total dot area ratio as referred to above is calculated from an area S1 of a subject region and a total area S2 of the dots present in the subject region according to the equation:

Total dot area ratio (%)=S2/S1×100

Figure 7:
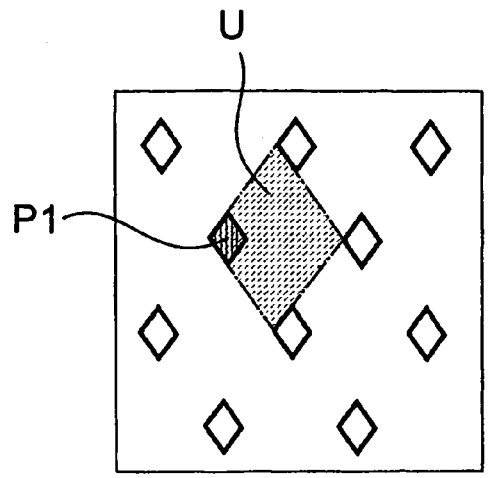
FIG. 7 represents the way of calculating a total dot area ratio.

While the "subject region" may be the whole of a region to be analyzed (e.g., the area M) in comparison with another region (e.g., the area S), it is advisable to extract such a part of the region (e.g., the area M) to be analyzed that would typically represent the dot distribution of that region in contrast to the dot distribution of another region to be compared with (e.g., the area S). For example, in case where dots are arranged in the areas M and S with respective regularity as illustrated in FIG. 7, a smallest unit U of the pattern (a smallest repeating unit U) is extracted, and a total dot area ratio in the unit U is calculated. In the example shown in FIG. 7, the total dot area ratio in the unit U is the area ratio (%) of a single dot P1 to the area of the unit U. The way of extracting a smallest unit U is not limited to that depicted in FIG. 7.

Considering that the influence of the dots on the main pattern 81 should be minimized, the total dot area ratio in the region having the main pattern 81 (i.e., the middle area M) is preferably 0 to 25%, more preferably 0 to 7%. The total dot area ratio in the region with no main pattern (i.e., the two side areas S) is preferably 1 to 90%, more preferably 7 to 30%.

Note that the above-recited total dot area ratios are those calculated based on the smallest unit of the pattern in the respective regions. The ratio of the total dot area ratio (a %) in a region having the main pattern to the total dot area ratio (b %) in a region having no main pattern (a/b) is preferably smaller than 0.9, more preferably smaller than 0.3, most preferably smaller than 0.1

In the particular examples shown in FIGS. 6(*a*), 6(*c*), and 6(*d*), all the dots are equal in area, and the area of the individual dots ranges from 0.001 to 30 mm².

Arrangement (3):

Dots 82 corresponding to the projections 82 are distributed substantially uniformly all over the patterned sheet 8. See FIG. 6(*d*).

FIG. 6(*d*) presents a preferred example of the arrangement (3). The dots 82 are distributed almost uniformly in a rhombic lattice pattern over the area including the region having the main pattern 81 (the middle area M) and the regions with no main pattern (the two side areas S).

The dots 82 corresponding to the projections in the patterned sheet of the front portion A and/or the rear portion B preferably have any one of the above-described patterns of arrangement in the diaper length direction within the area wherein the below-waist elastic members are dispersed (including the area where the cut ends and fragments exist).

After cutting the below-waist elastic members, an absorbent body 10 separately prepared in a usual manner is put on the exterior laminate of continuous form as shown in FIG. 4. The resulting laminate structure of continuous form is then fabricated in a known manner (e.g., cutting to product size, cutting off unnecessary parts corresponding to leg openings, and joining the front and rear portions A and B at their side edges) to produce the disposable pull-on diaper 1.

Materials of the above-described diaper constituting members will be described hereunder.

The outer sheet 21 can be of any materials that allow the pattern of the patterned sheet 8 be seen through from the outside. Nonwoven fabric is preferably used. Resin films transparent to light are also employable.

For securing clear see-through visibility of the pattern from the outside and user-attractive appearance, it is preferred for the outer sheet 21 to have a total transmittance of 55% or higher, more preferably 65% or higher, most preferably 75% or higher. The see-through visibility of the pattern reduces with a decrease in total transmittance.

Total transmittance is measured with a reflectance and transmittance meter HR-100 supplied by Murakami Color Research Lab. A total transmittance $T_t$ is measured using CIE illuminance A. Measurement is made on arbitrarily selected 10 points of a sample sheet to obtain an average. The total transmittance of nonwoven fabric hardly varies depending on the process of fabrication and is rather governed by the basis weight. A preferred basis weight for obtaining high total transmittance is 40 g/m$^2$ or less, more preferably 30 g/m$^2$ or less. Taking softness, touch, and cost into consideration as well as sufficient strength, a preferred basis weight of nonwoven fabric used as an outer sheet is 5 to 30 g/m$^2$.

The nonwoven fabric for use as an outer sheet can be selected from various kinds commonly used in such absorbent articles as disposable diapers and sanitary napkins, including spun bonded nonwoven, melt blow nonwoven, spun laced nonwoven, needle punched nonwoven, and laminates composed of two or more thereof. Fibers making up the nonwoven fabric include synthetic fibers of polyolefins (e.g., polyethylene and polypropylene), polyesters (e.g., polyethylene terephthalate), and polyamides (e.g., nylon); regenerated cellulosic fibers, such as rayon and cuprammonium; and natural fibers, such as cotton. Sheath-core conjugate fibers having high-melting fiber as a core and low-melting fiber as a sheath and side-by-side conjugate fibers are also suitable. These fibers can be used either individually or as a combination of two or more thereof.

The inner sheet 22 can be of any materials commonly used in such absorbent articles as disposable diapers and sanitary napkins, including the above-recited nonwoven fabrics, resin film, and composites of nonwoven fabric and resin film.

The patterned sheet 8 can be made of any materials commonly used in such absorbent articles as disposable diapers and sanitary napkins, including the above-recited nonwoven fabrics, resin film, and composites of nonwoven fabric and resin film. The resin film is preferably permeable to moisture. The pattern 81 of the patterned sheet 8 is provided by printing by various known printing apparatus or other methods such as stitching or weaving with color yarn. It is desirable for nonwoven fabric to be printed to have a smooth surface for providing clear design.

The patterned sheet 8 is preferably made of moisture permeable film or nonwoven fabric, taking into consideration softness, breathability, pattern visibility, ability to hide the cut ends and fragments of elastic members, strength against pressing with projections, and material cost. The patterned sheet 8 may be either liquid permeable as in the above-mentioned embodiment or liquid impermeable as in a second embodiment described later.

Where weight is put on breathability, the patterned sheet 8 is preferably made of nonwoven fabric (e.g., air through nonwoven or spun bonded nonwoven) having a basis weight of 5 to 40 g/m$^2$. Breathability reduces with an increase in basis weight. Melt blown nonwoven fabric tends to have poor breathability.

The manner of applying an adhesive to the patterned sheet 8 is another important factor for securing sufficient see-through visibility and maintaining softness and breathability of the patterned sheet. Of various methods of applying hot-melt adhesives, solid coating impairs softness and breathability. Methods assuring good balance among adhesion, softness, and breathability are favorable. From this viewpoint, the hot-melt adhesive is preferably applied in a spiral pattern, a zig-zag pattern or an omega pattern.

The below-waist elastic members 23 can be of various known elastic materials. Useful elastic materials include synthetic rubbers, such as styrene-butadiene rubber, butadiene rubber, isoprene rubber, and neoprene rubber; natural rubber; ethylene-vinyl acetate copolymers, extensible polyolefins, and urethane rubber. Spandex elastic fiber is preferred of them. The elastic member may be a thread having a rectangular, square, circular or polygonal cross-section, a multifilament elastic yarn, or an elastic strip or tape. Elastic materials which are plasticized by heat are also suited. It is particularly preferred to use two or more strands of spandex multi-filament yarn, especially with a fineness of 80 to 620 dtex, in a 2 to 5 times stretched state.

Where spandex multi-filament yarn is used as a below-waist elastic member, the adhesiveness of the yarn can be controlled by adjusting the amount of finishing oil applied thereto. Finishing oil is used to improve surface smoothness (slip) of yarn for reducing stickiness in reeling, facilitating unreeling, and stabilizing subsequent processing. Application of too much finishing oil results in reduction of adhesiveness retention. Adequate adhesiveness can be secured by applying finishing oil in an amount of not more than 5%, preferably 2% or less. When the adhesiveness of the below-waist elastic members is to be controlled, for example, when the adhesiveness is to be reduced so that the below-waist elastic members may easily be let free when cut in the region corresponding to a main pattern, which is favorable for appearance, the amount of finishing oil to be applied can be increased. Such being the case, the amount of the finishing oil to be applied is preferably selected from the range from 0 to 10% by weight, more preferably 0.2 to 7% by weight, based on the spandex elastic yarn, according to the thickness of the yarn and the stretch ratio of the yarn when fixed.

Materials of the other members, such as the topsheet 2, the backsheet 3, the absorbent member 4, and the standing cuffs 7, are arbitrarily selected from among those commonly employed in disposable diapers, sanitary napkins, and the like.

Figure 8:
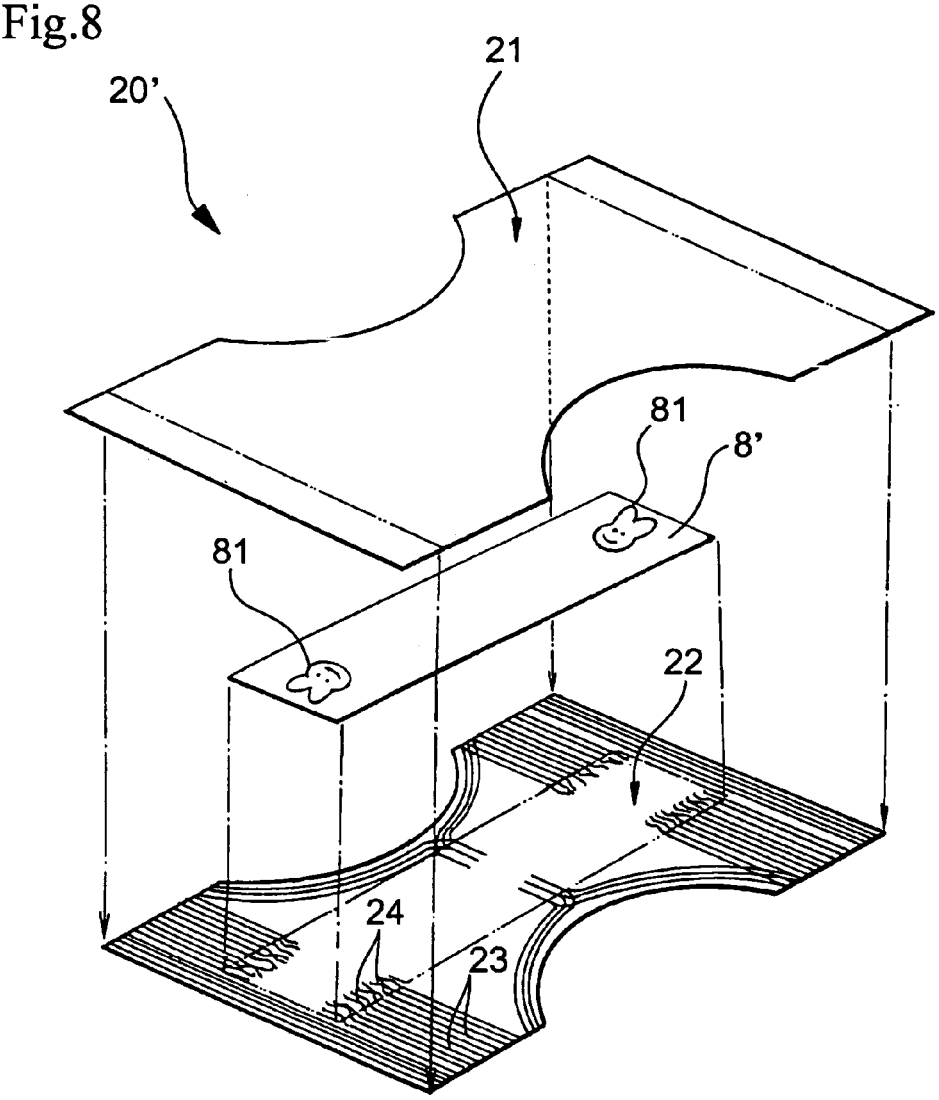
FIG. 8 is an exploded perspective view of the exterior laminate of a disposable diaper according to another embodiment of the present invention (corresponding to FIG. 3).

A disposable diaper of the second embodiment of the absorbent article according to the present invention will now be illustrated by way of FIG. 8. The difference of the second embodiment from the first one resides in that a patterned sheet 8' has a length extending from the below-waist portion D of the front portion A to the below-waist portion D of the rear portion B, the patterned sheet 8' is impermeable to liquid, and the absorbent body has no backsheet. The second embodiment will be described only with reference to the difference. The description of the first embodiment applies appropriately to those particulars that are not referred to here.

FIG. 8 is a perspective of an external laminate 20' used in the second embodiment in its exploded state. As shown, the patterned sheet 8' extends from the below-waist portion D of the front portion A to the below-waist portion D of the rear portion B. A pictorial pattern 81, which is seen through the outer sheet 21, is printed on the regions corresponding to the below-waist portions D of the front and rear portions A and B. The patterned sheet 8' has a patterned region that is to be disposed in the below-waist portion D of the front portion A and a patterned region that is to be disposed in the below-waist portion D of the rear portion B. These two patterned regions function in the same manner as the two patterned sheets 8 of the first embodiment. Accordingly, the disposable diaper according to the second embodiment produces the same effects as in the first one. The patterned sheet 8' may have a pattern printed over its whole length.

Because the patterned sheet 8' is liquid impermeable, a part or the whole of the liquid impermeable backsheet used in the first embodiment may be omitted. The patterned sheet 8' used in this particular example has a larger contour than the absorbent member of the absorbent body to be combined with, so that the absorbent body is not provided with a liquid impermeable backsheet.

The disposable diaper of the second embodiment can be produced more efficiently and more economically than that of the first embodiment. That is, the patterned sheet 8' is placed with spacing on the area including both below-waist portions D of the front and rear portions A and B instead of placing two patterned sheets 8 with spacing on the respective areas, and an absorbent body with no backsheet 3 is used in place of the absorbent body 10 containing the backsheet 3.

While the present invention has been described with reference to particular embodiments thereof, it will be understood that various changes and modifications can be made therein without departing from the spirit and scope thereof. For instance, the disposable diaper of the first embodiment may have only one patterned sheet on either the front portion A or the rear portion B. It is preferred that the below-waist elastic members 23 in the regions outside the lateral sides of the patterned sheet be fixed along the diaper width direction over their whole length in the respective regions, but they do not always need to be fixed over their whole length in the respective regions. There may be only cut ends, but no fragments, of the below-waist elastic members 23 in the region inside the lateral sides of the patterned sheet. The disposable diaper may have the below-waist elastic members only in one of the front and rear portions A and B. The disposable diaper may have the elastic members 23 for providing a below-waist gather only in one of the front and rear portions A and B. One or a few of the elastic members 23 for a below-waist gather may be disposed continuously in the diaper width direction without being separated into two side portions.

The absorbent article of the present invention includes not only the disposable pull-on diapers but other pull-on absorbent articles, such as shorts-type napkins, and disposable fitted diapers having a gather in the below-waist portion in the rear portion. The below-waist portion in a fitted diaper is a portion below the portion where a waist elastic member is fixed and above the crotch portion providing leg openings.

With respect to particulars that have not been described for one embodiment, the details of other embodiments appropriately apply, and the factors possessed by one embodiment appropriately apply to other embodiments. Factors of each of the aforementioned embodiments are interchangeable with each other.

The absorbent article according to the present invention has a pattern that can be clearly seen through from the outside. Made up of a fewer number of constituent members, the absorbent article of the invention can be produced efficiently and economically.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article having a front portion and a rear portion and comprising an outer sheet that provides an outer surface of the absorbent article, an inner sheet disposed on the inner side of the outer sheet, and a plurality of elastic members for making below-waist gathers disposed between the outer sheet and the inner sheet, wherein a patterned sheet having a pattern is disposed between the outer sheet and the inner sheet in the widthwise middle area of at least one of the front portion and the rear portion, the elastic members each have:
  (a) a portion contributory to elastic extensibility and contractibility in each of the regions outside the lateral sides of the patterned sheet; and
  (b) a portion substantially non-contributory to elastic extensibility and contractibility that are cut fragments of adjacent elastic members that contribute to elastic extensibility and contractibility, and which are separate and distinct fragments from the adjacent elastic member from which they are cut, disposed between the patterned sheet and the inner sheet in the region inside the lateral sides of the pattered sheet; and wherein the cut fragments of elastic members are formed by pressing elastic members of continuous length together with the patterned sheet and the outer sheet with a pressing member having projections providing dots.

2. The absorbent article according to claim 1, wherein the outer sheet has a total transmittance of 55% or higher.

3. The absorbent article according to claim 1, wherein the cut fragments are formed by pressing elastic members of continuous length together with the patterned sheet with a pressing member having projections providing dots, the projections being arranged only in the area where a main pattern of the patterned sheet is absent.

4. The absorbent article according to claim 1, wherein the cut fragments are formed by pressing elastic members of continuous length together with the patterned sheet with a pressing member having projections providing dots, the projections being arranged in both the area where a main pattern of the patterned sheet is present and the area where the main pattern is absent, the individual dots having an area of 0.001 to 30 mm$^2$, and the total dot area ratio in the area where the main pattern is present being lower than that in the area where the main pattern is absent.

5. The absorbent article of claim 1, wherein the cut fragments are formed by pressing elastic members of continuous length together with the patterned sheet with a pressing member having projections providing dots, the projections being arranged substantially uniformly over the entire area of the patterned sheet.

6. The absorbent article according to claim 1, which is a pull-on absorbent article.

7. The absorbent article according to claim 1, wherein the outer sheet is a nonwoven fabric.

8. The absorbent article according to claim 7, wherein the nonwoven fabric has a basis weight of 5 to 30 g/mm$^2$.

9. A process of producing the absorbent article according to claim 1, comprising the steps of disposing a patterned sheet at an interval on a running outer sheet of continuous length, continuously introducing elastic members of continuous length between the outer sheet with the patterned sheet on and a running inner sheet of continuous length, bonding the inner sheet to the patterned sheet side of the outer sheet, to form a laminate, and cutting the elastic members of continuous length by pressing a pressing member having projections against the region where the patterned sheet is disposed.

10. The absorbent article according to claim 1, wherein a hot-melt adhesive is over a stock sheet except for the region inside the lateral sides of each patterned sheet where the below-waist elastic members are disposed or the adhesive is over the stock sheet except that the amount of the adhesive applied to the region inside the lateral sides of each patterned sheet where the below-waist elastic members are disposed is reduced as compared with the lateral regions.

11. The absorbent article according to claim 1, wherein the elastic members of continuous length are cut at two or more positions in the portion substantially non-contributory to elastic extensibility and contractibility to form said cut fragments.

12. The absorbent article according to claim 1, wherein the inner sheet is provided with an adhesive over the surface on the outer sheet side, while the region outside the lateral sides of each patterned sheet is provided with the adhesive, the region inside the lateral sides of each patterned sheet is not provided with the adhesive or is provided with a reduced amount of the adhesive as compared with the region outside the lateral sides of each patterned sheet.

13. The absorbent article according to claim 1, wherein the front portion and the rear portion are provided with the patterned sheet, the patterned sheet is a single continuous sheet which extends from the below-waist portion of the front portion to the below-waist portion of the rear portion.

14. The absorbent article according to claim 1, wherein the patterned sheet 8 is impermeable to liquid.

* * * * *